US011897977B2

(12) United States Patent
Moser et al.

(10) Patent No.: US 11,897,977 B2
(45) Date of Patent: Feb. 13, 2024

(54) PHOTOLABILE BARBITURATE COMPOUNDS

(71) Applicant: 3M INNOVATIVE PROPERTIES COMPANY, St. Paul, MN (US)

(72) Inventors: William H. Moser, Edina, MN (US); Erik M. Townsend, Hastings, MN (US); Zachary J. Thompson, Woodbury, MN (US); Mary M. Caruso Dailey, Maplewood, MN (US); Michael A. Kropp, Cottage Grove, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 635 days.

(21) Appl. No.: 16/965,688

(22) PCT Filed: Jan. 16, 2019

(86) PCT No.: PCT/US2019/013726
§ 371 (c)(1),
(2) Date: Jul. 29, 2020

(87) PCT Pub. No.: WO2019/152187
PCT Pub. Date: Aug. 8, 2019

(65) Prior Publication Data
US 2021/0040240 A1 Feb. 11, 2021

Related U.S. Application Data

(60) Provisional application No. 62/624,158, filed on Jan. 31, 2018.

(51) Int. Cl.
| | | |
|---|---|---|
| *C08F 2/50* | (2006.01) | |
| *C08F 220/18* | (2006.01) | |
| *C07D 239/62* | (2006.01) | |
| *C07D 405/12* | (2006.01) | |

(52) U.S. Cl.
CPC .............. *C08F 2/50* (2013.01); *C07D 239/62* (2013.01); *C07D 405/12* (2013.01); *C08F 220/1802* (2020.02)

(58) Field of Classification Search
CPC ........ C08F 2/50; C08F 220/1802; C08F 2/48; C08F 220/10; C08F 2/44; C08F 4/40; C08F 220/281; C08F 222/10; C07D 239/62; C07D 405/12; C08K 3/013; C08L 33/08; C09J 7/10; C09J 7/385; C09J 2301/408; C09J 2433/00
See application file for complete search history.

(56) References Cited

U.S. PATENT DOCUMENTS

| | | |
|---|---|---|
| 2,801,185 A | 7/1957 | Iler |
| 3,347,954 A | 10/1967 | Bredereck |
| 3,496,250 A | 2/1970 | Czerwinski |
| 4,503,169 A | 3/1985 | Randklev |
| 4,522,958 A | 6/1985 | Das |
| 4,576,976 A * | 3/1986 | Schaefer ................ A61K 6/887 522/63 |
| 5,657,402 A | 8/1997 | Bender |
| 5,920,657 A | 7/1999 | Bender |
| 6,586,483 B2 | 7/2003 | Kolb |
| 7,074,839 B2 | 7/2006 | Fansler |
| 7,090,721 B2 | 8/2006 | Craig |
| 7,090,722 B2 | 8/2006 | Budd |
| 7,156,911 B2 | 1/2007 | Kangas |
| 7,235,775 B2 | 6/2007 | Masaki |
| 7,342,047 B2 | 3/2008 | Lewandowski |
| 7,542,821 B2 | 6/2009 | Floeder |
| 7,598,298 B2 | 10/2009 | Lewandowski |
| 7,623,699 B2 | 11/2009 | Floeder |
| 7,649,029 B2 | 1/2010 | Kolb |
| 7,797,133 B2 | 9/2010 | Floeder |
| 7,974,459 B2 | 7/2011 | Floeder |
| 9,322,786 B2 | 4/2016 | Takami |
| 9,719,939 B2 | 8/2017 | Krebs |
| 2006/0071156 A1 | 4/2006 | Masaki |
| 2007/0057208 A1 | 3/2007 | Joss |
| 2009/0159799 A1 | 6/2009 | Copeland |
| 2011/0043691 A1 | 2/2011 | Guitteny |
| 2011/0069878 A1 | 3/2011 | Case |
| 2015/0284601 A1 | 10/2015 | Yurt |
| 2016/0185993 A1 | 6/2016 | Yoshida |
| 2016/0213577 A1 | 7/2016 | Matsumoto et al. |
| 2016/0369115 A1 | 12/2016 | Shimoju |

FOREIGN PATENT DOCUMENTS

| | | |
|---|---|---|
| CN | 103049413 | 4/2013 |
| DE | 3639636 | 5/1988 |
| DE | 102012101310 | 4/2013 |

(Continued)

OTHER PUBLICATIONS

Machine English translation of JP 2006-183013 (Year: 2006).*
Klan, "Photoremovable Protecting Groups in Chemistry and Biology: Reaction Mechanisms and Efficiency", Chem Reviews, 2013, vol. 113, pp. 119-191.
Matyjaszewski, "Atom transfer radical polymerization", Chem. Rev., 2001, vol. 101, pp. 2921-2990.
Pelliccioli, "Photoremovable protecting groups: reaction mechanisms and applications", Photochem Photobiol Sci.,2002, vol. 1, pp. 441-458.
Seibert, "Flat field correction technique for digital detectors", Medical Imaging 1998: Physics of medical imaging, 1998, vol. 3336, pp. 348-354.

(Continued)

*Primary Examiner* — Jessica M Roswell

(57) ABSTRACT

The present disclosure provides a redox initiator system for initiating polymerization comprising an oxidizing agent, a photolabile reducing agent derived from a barbiturate, and a transition metal complex that participates in a redox cycle. On exposure to actinic radiation, such as UV, the photolabile compound photolyzes, releasing the reducing agent and initiating the redox-initiated polymerization.

17 Claims, No Drawings

(56) References Cited

FOREIGN PATENT DOCUMENTS

| | | |
|---|---|---|
| EP | 0052813 | 6/1982 |
| EP | 1348946 | 10/2003 |
| EP | 1712897 | 10/2006 |
| EP | 2177947 | 4/2010 |
| EP | 2208355 | 7/2010 |
| JP | 63290867 | 11/1988 |
| JP | 2006183013 A | 7/2006 |
| WO | WO 2007-140440 | 12/2007 |
| WO | WO 2008-024611 | 2/2008 |
| WO | WO 2009-014940 | 1/2009 |
| WO | WO 2014-078115 | 5/2014 |
| WO | WO 2014-151650 | 9/2014 |
| WO | WO 2014-172530 | 10/2014 |
| WO | WO 2015-200007 | 12/2015 |
| WO | WO 2016-014218 | 1/2016 |
| WO | WO 2016-044151 | 3/2016 |
| WO | WO 2016-053877 | 4/2016 |
| WO | WO 2016-137317 | 9/2016 |
| WO | WO 2017-095704 | 6/2017 |
| WO | WO 2018-215889 | 11/2018 |
| WO | WO 2019-150242 | 8/2019 |
| WO | WO 2019-150243 | 8/2019 |
| WO | WO 2019-152267 | 8/2019 |

OTHER PUBLICATIONS

Senda, "Uracil derivatives and related compounds IX Synthesis of Bucolomes related compounds" 1969, vol. 89, pp. 266-271.
Sidky, "Organophosphorous compounds. XXV Reactivity of Benzlidenebarbituric Acid Towards Tervalent Phosphorous Compounds" Egypt J. Chem, 1978, vol. 21, No. 1, pp. 37-46.
Wu, "Mode of Action of 4-Hydroxyphenylpyruvate Dioxygenase Inhibition by Triketone-type Inhibitors", J. Med. Chem., 2002, vol. 45, pp. 2222-2228.
Xu, "Industrial web inspection for manufacturing process understanding and control", Machine vision application in industrial inspection, 1999, vol. 3652, pp. 10-20.
Yong, "Photochemistry of 2-Nitrobenzyl Enol Ethers: Oxidative C=C Bond Scission", Org. Lett., 2005, vol. 7, No. 12, pp. 2485-2487.
International Search report for PCT International Application No. PCT/US2019/013726 dated May 7, 2019, 6 pages.

\* cited by examiner

PHOTOLABILE BARBITURATE COMPOUNDS

CROSS REFERENCE TO RELATED APPLICATIONS

This application is a national stage filing under 35 U.S.C. § 371 of PCT/US2019/013726, filed Jan. 16, 2019, which claims the benefit of Provisional Application No. 62/624,158, filed Jan. 31, 2018, the disclosure of which is incorporated by reference in its/their entirety herein.

BACKGROUND

Redox reactions represent an important method for initiating the curing of acrylate, methacrylate and other vinyl-based resin, including adhesive formulations. Redox-initiated curing often has advantages over photoinitiated curing, including improved depth of cure and a slower accumulation of stress during the initial stages of curing.

A significant challenge in the use of redox initiating systems is finding an optimal balance between stability and reactivity. The reactivity of the redox system needs to be sufficiently high for full curing and attainment of mechanical properties within a short period of time. However, if the reactivity is too great, problems such as premature curing, accumulation of stress, and poor shelf stability of the formulation can be encountered.

Free-radical polymerization of vinyl compound(s) using certain beta-dicarbonyl (i.e., 1,3-dicarbonyl) compounds in the presence of a peroxide and/or oxygen, a halide salt, and a copper compound such as copper acetylacetonate, has been described in U.S. Pat. No. 3,347,954 (Bredereck et al.). Such compositions cause free-radical polymerization of the vinyl compound(s) over time, with shorter times generally being preferred. Since the compositions are spontaneously reactive, it is common practice to provide them as a two-part system such as, for example, a part A and a part B that are combined immediately prior to use.

SUMMARY

Applicants provide a method to overcome these problems by creating an "on demand" redox-initiated cure, in which the reducing agent of the redox cure initiator system has latent activity while the formulation is stored and delivered, but then can be triggered when required.

The present disclosure provides a redox initiator system for initiating polymerization comprising an oxidizing agent, a photolabile reducing agent, and a transition metal complex that participates in a redox cycle. On exposure to actinic radiation, such as UV, the photolabile compound photolyzes, generating the reducing agent and initiating the redox-initiated polymerization. Advantageously, polymerization of the instant compositions may be initiated by exposure to actinic radiation, but continued irradiation is not required. When the redox initiator system is combined with polymerizable component monomers or oligomers to form a polymerizable composition, the polymerization may be initiated, then build molecular weight and physical properties as the composition continues to cure in the absence of light.

In some embodiments the polymerizable compositions described herein combine the advantages of pressure sensitive adhesives (PSAs) and structural adhesives in the form of a one-part photo-triggered PSA-to-(semi)structural acrylic adhesive. This adhesive acts as a conventional PSA in its uncured or partially cured state, offering easy application, high wet-out, and green strength. The application of a short UV-light trigger initiates a radical-producing redox reaction that continues after the light is removed, inducing a steady rate of cure and a concomitant increase in cohesive strength. Finally, the cure will plateau at a level sufficient to give the adhesive structural or semi-structural performance.

In many embodiments the collection of properties and curing behavior would be especially useful in the common case of a permanent bond between two opaque substrates. In the absence of a UV trigger, the modulus of the adhesive lies below the level dictated by the Dahlquist criterion, meaning the material has tack and it can form a bond to a substrate with only the application of pressure. Next, the UV trigger is applied to the exposed face of the adhesive, initiating the self-sustaining redox reaction but leaving the surface tacky and able to wet out the second substrate within a reasonable period of time ("open time"). After bond closure, the adhesive continues to cure until its modulus reaches a level sufficient for structural strength.

In one aspect, this disclosure provides a polymerizable composition comprising one or more ethylenically-unsaturated polymerizable monomers or oligomers and an initiator system that participates in a reversible redox cycle upon irradiation.

In another aspect, this disclosure provides a structural adhesive composition comprising a multi-functional (meth)acrylate monomer comprising two (preferably three) or more (meth)acrylate groups, and/or a multi-functional (meth)acrylate oligomer and optionally a (meth)acrylate-functional diluent, and an initiator system that participates in a reversible redox cycle upon radiation.

DETAILED DESCRIPTION

The chemically polymerizable compositions include a polymerizable component (e.g., an ethylenically unsaturated polymerizable monomer or oligomer) and a redox initiator system that includes the transition metal complex, an oxidizing agent, and a photolabile reducing agent of the formula:

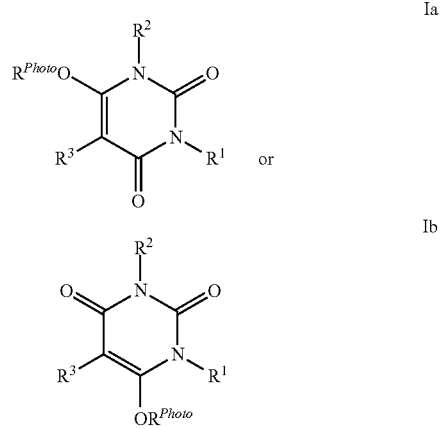

wherein
$R^1$, $R^2$ and $R^3$ are each independently H, $C_{1\text{-}18}$ hydrocarbyl; and
$R^{Photo}$ is a photolabile group. Isomers Ia and b will be considered functional equivalents.

$R^1$, $R^2$ and $R^3$ may independently represent a hydrocarbyl group, or a substituted-hydrocarbyl group, having from 1 to 18 carbon atoms. Preferably, $R^1$ and $R^2$ each have from 1 to 12 carbon atoms, more preferably 1 to 8 carbon atoms, and even more preferably 1 to 4 carbon atoms. Exemplary groups $R^1$ and $R^2$ include methyl, ethyl, isopropyl, n-propyl, butyl, pentyl, hexyl, octyl, decyl, dodecyl, hexadecyl, and octadecyl. Generally, the nature of the substituents in the substituted-hydrocarbyl groups (which may be mono-substituted or poly-substituted) is not particularly important, except that substituents that interfere with the free-radical polymerization should be used sparingly or excluded altogether. Exemplary substituted-hydrocarbyl groups include hydroxyhydrocarbyl groups (e.g., hydroxyethyl and hydroxypropyl), alkoxyhydrocarbyl groups (e.g., methoxyethyl and methoxyethoxy), alkanoylhydrocarbyl groups (e.g., acetylethyl and benzoylethyl), haloalkyl groups (e.g., chloroethyl and dichloropropyl), and dialkylaminohydrocarbyl groups (e.g., dimethylaminopropyl and diethylaminoethyl).

Examples of suitable barbituric acid derivatives of Formula Ia and b include those derived from 1,3,5-trimethylbarbituric acid, 1,3,5-triethylbarbituric acid, 1,3-dimethyl-5-ethylbarbituric acid, 1,5-dimethylbarbituric acid, 1-methyl-5-ethylbarbituric acid, 1-methyl-5-propylbarbituric acid, 5-ethylbarbituric acid, 5-propylbarbituric acid, 5-butylbarbituric acid, 1-benzyl-5-phenylbarbituric acid, and 1-cyclohexyl-5-ethylbarbituric acid.

Any known photolabile group ($R^{Photo}$ that may be irradiated and which cleaves or fragments to release the transition metal may be used. Reference may be made to Petr Klan et al., Photoremovable Protecting Groups in Chemistry and Biology: Reaction Mechanisms and Efficiency, *Chem Reviews*, 2013, Vol. 113, pp. 119-191 and Jacob Wirz et al., Photoremovable Protecting Groups: Reaction Mechanisms and Applications, *Photochem. Photobiol. Sci.*, 2002, Vol. 1, pp. 441-458.

With reference to Formula I, useful photolabile groups "$R^{photo}$" include, but are not limited to, phenacyl groups, 2-alkylphenacyl groups, ethylene-bridged phenacyl groups, o- or p-hydroxyphenacyl groups, benzoin groups, o-nitrobenzyl groups, o-nitro-2-phenethyloxycarbonyl groups, coumarin-4-yl methyl groups, benzyl groups, o-hydroxylbenzyl groups, o-hydroxynapthyl groups, 2,5-dihydroxyl benzyl groups, 9-phenylthioxanthyl, 9-phenylxanthyl groups, anthraquinon-2-yl groups, 8-halo-7-hydroxyquinoline-2-yl methyl groups, and pivaloylglycol groups.

The photolabile compounds of Formula I are generally prepared by means known in the art for preparing enol ethers or esters of beta-dicarbonyl compounds. In some embodiments the beta dicarbonyl compound may be treated with base or acid and the resulting enol/enolate then alkylated or esterified with the $R^{Photo}$ group. The compounds of Formulas Ia and b may be prepared by addition-elimination of the corresponding halo compounds.

The redox initiation system comprises a transition metal complex that participates in a redox cycle. Useful transition metal compounds have the general formula $[ML_p]^{n+}A^-$, wherein M is a transition metal that participates in a redox cycle, L is a ligand, A− is an anion, n is the formal charge on the transition metal having a whole number value of 1 to 7, preferably 1 to 3, and p is the number of ligands on the transition metal having a number value of 1 to 9, preferably 1 to 2.

Useful transition metals, M, include the catalytically active valent states of Cu, Fe, Ru, Cr, Mo, Pd, Ni, Pt, Mn, Rh, Re, Co, V, Au, Nb and Ag. Preferred low valent metals include Cu(II), Fe(II), Ru(II) and Co(II). Other valent states of these same metals may be used, and the active low valent state generated in situ.

Useful anions, $A^-$, include halogen, $C_1$-$C_6$ alkoxy, $NO_3^{2-}$, $SO_4^{2-}$, $PO_4^{3}$, $HPO_4^{2-}$, $PF_6$, triflate, hexafluorophosphate, methanesulfonate, arylsulfonate, $CN^-$, alkyl carboxylates and aryl carboxylates.

The ligand, L, is used to solubilize the transition metal salts in a suitable solvent and adjust the redox potential of the transition metal for appropriate reactivity and selectivity. The ligands can direct the metal complex to undergo the desired one-electron atom transfer process, rather than a two-electron process such as oxidative addition/reductive elimination. The ligands may further enhance the stability of the complexes in the presence of different monomers and solvents or at different temperatures. Acidic monomers and monomers that strongly complex transition metals may still be efficiently polymerized by appropriate selection of ligands.

Useful ligands include those having one or more nitrogen, oxygen, phosphorus and/or sulfur atoms which can coordinate to the transition metal through a σ-bond, ligands containing two or more carbon atoms which can coordinate to the transition metal through a π-bond, and ligands which can coordinate to the transition metal through a μ-bond or an η-bond.

Useful ligands include those having one or more nitrogen, oxygen, phosphorus and/or sulfur atoms which can coordinate to the transition metal through a σ-bond are provided by monodentate and polydentate compounds preferably containing up to about 30 carbon atoms and up to 10 heteroatoms selected from aluminum, boron, nitrogen, sulfur, non-peroxidic oxygen, phosphorus, arsenic, selenium, antimony, and tellurium, where upon addition to the metal atom, following loss of zero, one, or two hydrogens, the polydentate compounds preferably forming with the metal, $M^{n+}$, a 4-, 5-, or 6-membered saturated or unsaturated ring. Examples of suitable monodentate compounds or groups are carbon monoxide, alcohols such as ethanol, butanol, and phenol; pyridine, nitrosonium (i.e., $NO^+$); compounds of Group 15 elements such as ammonia, phosphine, trimethylamine, trimethylphosphine, tributylphosphine, triphenylamine, triphenylphosphine, triphenylarsine, tributylphosphite; nitriles such as acetonitrile, benzonitrile; isonitriles such as phenylisonitrile, butylisonitrile; carbene groups such as ethoxymethylcarbene, dithiomethoxycarbene; alkylidenes such as methylidene and ethylidene.

Suitable polydentate compounds or groups include dipyridyl, 1,2-bis(diphenylphosphino)ethane, 1,2-bis(diphenylarsino)ethane, bis(diphenylphosphino)methane, polyamines such as ethylenediamine, propylenediamine, tetramethyl ethylene diamine, hexamethyl tris-aminoethylamine, diethylenetriamine, 1,3-diisocyanopropane, and hydridotripyrazolylborate; the hydroxycarboxylic acids such as glycolic acid, lactic acid, salicylic acid; polyhydric phenols such as catechol and 2,2'-dihydroxybiphenyl; hydroxyamines such as ethanolamine, propanolamine, and 2-aminophenol; dithiocarbamates such as diethyldithiocarbamate, dibenzyldithiocarbamate; xanthates such as ethyl xanthate, phenyl xanthate; the dithiolenes such as bis(perfluoromethyl)-1,2-dithiolene; aminocarboxylic acids such as alanine, glycine and o-aminobenzoic acid; dicarboxylic diamines as oxalamide, biuret; diketones such as 2,4-pentanedione; hydroxyketones such as 2-hydroxyacetophenone; alpha-hydroxyoximes such as salicylaldoxime; ketoximes such as benzil oxime; 1,10-phenanthroline, porphyrin, cryptands and crown ethers, such as 18-crown-6 and glyoximes such as dimethylglyoxime.

Other suitable ligands that can coordinate to the transition metal through a σ-bond are the inorganic groups such as, for example, $F^-$, $OH^-$, $Cl^-$, $Br^-$, $I^-$, and $H^-$ and the organic groups such as, for example, $CN^-$, $SCN^-$, acetoxy, formyloxy, benzoyloxy, and the like. The ligand can also be a unit of a polymer; for example the amino group in poly(ethyleneamine); the phosphino group in poly(4-vinylphenyldiphenylphosphine); the carboxylic acid group in poly(acrylic acid); and the isonitrile group in poly(4-vinylphenylisonitrile).

Useful ligands containing two or more carbon atoms which can coordinate to the transition metal through a π-bond are provided by any monomeric or polymeric compound having an accessible unsaturated group, i.e., an ethylenic, —C=C— group; acetylenic, —C≡C— group; or aromatic group which has accessible π-electrons regardless of the total molecular weight of the compound.

Illustrative of π-bond ligands are the linear and cyclic ethylenic and acetylenic compounds having less than 100 carbon atoms (when monomeric), preferably having less than 60 carbon atoms, and from zero to 10 heteroatoms selected from nitrogen, sulfur, non-peroxidic oxygen, phosphorous, arsenic, selenium, boron, aluminum, antimony, tellurium, silicon, germanium, and tin, the ligands being those such as ethylene, acetylene, propylene, methylacetylene, α-butene, 2-butene, diacetylene, butadiene, 1,2-dimethylacetylene, cyclobutene, pentene, cyclopentene, hexene, cyclohexene, 1,3-cyclohexadiene, cyclopentadiene, 1,4-cyclohexadiene, cycloheptene, 1-octene, 4-octene, 3,4-dimethyl-3-hexene, and 1-decene; $\eta^3$-allyl, $\eta^3$-pentenyl, norbornadiene, $\eta^5$-cyclohexadienyl, cycloheptatriene, cyclooctatetraene, and substituted and unsubstituted carbocyclic and heterocyclic aromatic ligands having up to 25 rings and up to 100 carbon atoms and up to 10 hetero atoms selected from nitrogen, sulfur, non-peroxidic oxygen, phosphorus, arsenic, selenium, boron, aluminum, antimony, tellurium, silicon, germanium, and tin, such as, for example, $\eta^5$-cyclopentadienyl, benzene, mesitylene, toluene, xylene, tetramethylbenzene, hexamethylbenzene, fluorene, naphthalene, anthracene, chrysene, pyrene, $\eta^7$-cycloheptatrienyl, triphenylmethane, paracyclophane, 1,4-diphenylbutane, $\eta^5$-pyrrole, $\eta^5$-thiophene, $\eta^5$-furan, pyridine, gamma-picoline, quinaldine, benzopyran, thiochrome, benzoxazine, indole, acridine, carbazole, triphenylene, silabenzene, arsabenzene, stibabenzene, 2,4,6-triphenylphosphabenzene, $\eta^5$-selenophene, dibenzostannepine, $\eta^5$-tellurophene, phenothiazine, selenanthrene, phenoxaphosphine, phenarsazine, phenatellurazine, $\eta^5$-methylcyclopentadienyl, $\eta^5$-pentamethylcyclopentadienyl, and 1-phenylborabenzene. Other suitable aromatic compounds can be found by consulting any of many chemical handbooks.

Preferred ligands include unsubstituted and substituted pyridines and bipyridines, tertiary amines, including polydentate amines such as tetramethyl ethylenediamine and hexamethyl tris-aminoethylamine, acetonitrile, phosphites such as $(CH_3O)_3P$, 1,10-phenanthroline, porphyrin, cryptands and crown ethers, such as 18-crown-6. The most preferred ligands are polydentate amines, bipyridine and phosphites. Useful ligands and ligand-metal complexes useful in the initiator systems of the present invention are described in Matyjaszewski and Xia, *Chem. Rev., Vol.* 101, pp. 2921-2990, 2001.

The molar proportion of photolabile reducing agent (of Formula I) relative to the transition metal complex is generally that which is effective to polymerize the selected polymerizable component(s), but may be from 1000:1 to 5:1, preferably from 500:1 to 25:1, more preferably from 250:1 to 50:1, and most preferably from 200:1 to 75:1. The oxidant and photolabile reductant of the redox initiator system are used in approximately equimolar amount. Generally the mole ratio of the oxidant and photolabile reductant is from 1:1.5 to 1.5:1, preferably 1:1.1 to 1.1 to 1.

Suitable oxidizing agents will also be familiar to those skilled in the art, and include but are not limited to persulfuric acid and salts thereof, such as sodium, potassium, ammonium, cesium, and alkyl ammonium salts. Preferred oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the photolabile reducing agent is present in an amount of at least 0.01 part by weight, and more preferably at least 0.1 part by weight, based on the total weight of the monomer components of the polymerizable composition. Preferably, the reducing agent is present in an amount of no greater than 10 parts by weight, and more preferably no greater than 5 parts by weight, based on the total weight of the polymerizable components of the polymerizable composition.

Preferably, the oxidizing agent is present in an amount of at least 0.01 part by weight, and more preferably at least 0.10 parts by weight, based on the total weight of the polymerizable components of the polymerizable composition. Preferably, the oxidizing agent is present in an amount of no greater than 10 part by weight, and more preferably no greater than 5 parts by weight, based on the total weight of the polymerizable components of the polymerizable composition.

The curable composition optionally comprises a quaternary ammonium halide that may accelerate the free-radical polymerization rate. Suitable quaternary ammonium halides include those having four hydrocarbyl (e.g., alkyl, alkenyl, cycloalkyl, aralkyl, alkaryl, and/or aryl) groups. Preferably, the hydrocarbyl groups are independently selected from hydrocarbyl groups having from 1 to 18 carbon atoms, more preferably 1 to 12 carbon atoms, and more preferably 1 to 4 carbon atoms. Examples of suitable hydrocarbyl groups include methyl, ethyl, propyl, butyl, hexyl, octyl, dodecyl, hexadecyl, and octadecyl, benzyl, phenyl, tolyl, cyclohexyl, and methylcyclohexyl. Exemplary suitable quaternary ammonium compounds include tetramethylammonium halides, tetraethylammonium halides, tetrapropylammonium halides, tetrabutylammonium halides, ethyltrimethylammonium halides, diethyldimethylammonium halides, trimethylbutylammonium halides, trioctylmethylammonium halides, and benzyltributylammonium halides. Any halide (e.g., F, Cl, Br, I) ion may be used in the quaternary ammonium halide, but preferably the halide ion is chloride or bromide.

The quaternary ammonium salt may be present in the curable composition in any amount, but preferably in an amount of from 0.01 to 5 percent by weight, preferably 0.1 to 2 percent although other amounts may also be used relative to 100 parts of the polymerizable monomers.

The present disclosure further provides a polymerizable composition comprising the redox initiator system (including transition metal complex, oxidant and photolabile reductant), and at least one polymerizable component monomer, such as vinyl monomers, and (meth)acryloyl monomers (including acrylate esters, amides, and acids to produce (meth)acrylate homo- and copolymers). The redox initiator system is present in the composition in amounts, from about 0.1 to about 10 parts by weight, preferably 0.1 to 5 parts by weight, based on 100 parts by weight of the polymerizable component of the polymerizable composition.

In some embodiments, the polymerizable composition comprises the redox initiator system and one or more vinyl monomers. Vinyl monomers useful in the polymerizable composition include vinyl ethers (e.g. methyl vinyl ether, ethyl vinyl ether), vinyl esters (e.g., vinyl acetate and vinyl propionate), styrene, substituted styrene (e.g., α-methyl styrene), vinyl halide, divinylbenzene, alkenes (e.g. propylene, isomers of butylene, pentene, hexylene up to dodecene, isoprene, butadiene) and mixtures thereof.

In some embodiments the polymerizable composition comprises one or more (meth)acrylate ester monomer(s). (Meth)acrylate ester monomers useful in preparing (meth)acrylate (co)polymers are monomeric (meth)acrylic esters of a non-tertiary alcohols, wherein the alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctylalcohol, 2-ethyl-1-hexanol, 1-decanol, 2-propylheptanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomers are suitable. In some embodiments, the preferred (meth)acrylate ester monomer is the ester of (meth)acrylic acid with an alcohol derived from a renewable source, such as 2-octanol, citronellol, or dihydrocitronellol.

In some embodiments it is desirable for the (meth)acrylic acid ester monomer to include a high glas transition ($T_g$) monomer. The homopolymers of these high $T_g$ monomers have a $T_g$ of at least 25° C., and preferably at least 50° C. Examples of suitable monomers useful in the present invention include, but are not limited to, t-butyl acrylate, methyl methacrylate, ethyl methacrylate, isopropyl methacrylate, n-butyl methacrylate, isobutyl methacrylate, s-butyl methacrylate, t-butyl methacrylate, stearyl methacrylate, phenyl methacrylate, cyclohexyl methacrylate, isobornyl acrylate, isobornyl methacrylate, benzyl methacrylate, 3,3,5 trimethylcyclohexyl acrylate, cyclohexyl acrylate, N-octyl acrylamide, and propyl methacrylate or combinations.

The (meth)acrylate ester monomer is present in an amount of up to 100 parts by weight, preferably 85 to 99.5 parts by weight based on 100 parts total monomer content used to prepare the polymer, exclusive of the amount of multifunctional (meth)acrylates. Preferably (meth)acrylate ester monomer is present in an amount of 90 to 95 parts by weight based on 100 parts total monomer content. When high $T_g$ monomers are included, the copolymer may include up to 50 parts by weight, preferably up to 20 parts by weight of the (meth)acrylate ester monomer component.

The polymerizable composition may comprise an acid functional monomer, where the acid functional group may be an acid per se, such as a carboxylic acid, or a portion may be a salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic or phosphoric acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids. The acid functional monomer is generally used in amounts of 0.5 to 15 parts by weight, preferably 1 to 15 parts by weight, most preferably 5 to 10 parts by weight, based on 100 parts by weight total monomer.

The polymerizable composition may comprise a polar monomer. The polar monomers useful in preparing the copolymer are both somewhat oil soluble and water soluble, resulting in a distribution of the polar monomer between the aqueous and oil phases in an emulsion polymerization. As used herein the term "polar monomers" are exclusive of acid functional monomers.

Representative examples of suitable polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; tetrahydrofurfuryl (meth)acrylate, poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of tetrahydrofurfuryl (meth)acrylate, 2-hydroxyethyl (meth)acrylate and N-vinylpyrrolidinone. The polar monomer may be present in amounts of 0 to 10 parts by weight, preferably 0.5 to 5 parts by weight, based on 100 parts by weight total monomer.

The polymerizable composition may further comprise a vinyl monomer when preparing acrylic copolymers. When used, vinyl monomers useful in the (meth)acrylate polymer include vinyl esters (e.g., vinyl acetate and vinyl propionate), styrene, substituted styrene (e.g., α-methyl styrene), vinyl halide, divinylbenzene, and mixtures thereof. As used herein vinyl monomers are exclusive of acid functional monomers, acrylate ester monomers and polar monomers. Such vinyl monomers are generally used at 0 to 5 parts by weight, preferably 1 to 5 parts by weight, based on 100 parts by weight total monomer when preparing acrylic copolymers.

A multifunctional (meth)acrylate may be incorporated into the blend of polymerizable monomers. Examples of useful multifunctional (meth)acrylates include, but are not limited to, di(meth)acrylates, tri(meth)acrylates, and tetra (meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth) acrylate is tailored depending upon application of the adhesive composition, for example, adhesives, or hardcoats.

Typically, the multifunctional (meth)acrylate is present in amounts up to 100 parts, preferably 0.1 to 100 parts, based 100 parts by weight of remaining polymerizable monofunctional monomers. In some embodiments the multifunctional (meth)acrylate is used in amounts of greater than 50 parts by weight, based on the 100 parts by weight of remaining polymerizable monomers. In some embodiments, the multifunctional (meth)acrylate may be present in amounts from 0.01 to 5 parts, preferably 0.05 to 1 parts, based on 100 parts total monomers of the polymerizable composition for adhesive applications, and greater amounts for hardcoats.

In such embodiments, an acrylic copolymer may be prepared from a polymerizable composition comprising:
  i. up to 100 parts by weight, preferably 85 to 99.5 parts by weight of an (meth)acrylic acid ester;
  ii. 0 to 15 parts by weight, preferably 0.5 to 15 parts by weight of an acid functional ethylenically unsaturated monomer;
  iii. 0 to 15 parts by weight of a non-acid functional, ethylenically unsaturated polar monomer;
  iv. 0 to 5 parts by weight vinyl monomer;
  v. 0 to 100 parts by weight of a multifunctional (meth) acrylate, preferably 50 to 100 parts by weight, relative to i-iv; and
  vi. the redox initiator system (including the complex, oxidant and photolabile reductant) in amounts from about 0.1 weight percent to about 5.0 weight percent, relative to 100 parts total monomer i-v.

The polymerizable composition may also include other additives. Examples of suitable additives include tackifiers (e.g., rosin esters, terpenes, phenols, and aliphatic, aromatic, or mixtures of aliphatic and aromatic synthetic hydrocarbon resins), surfactants, plasticizers (other than physical blowing agents), nucleating agents (e.g., talc, silica, or $TiO_2$), pigments, dyes, reinforcing agents, solid fillers, stabilizers (e.g., UV stabilizers), and combinations thereof. The additives may be added in amounts sufficient to obtain the desired properties for the cured composition being produced. The desired properties are largely dictated by the intended application of the resultant polymeric article.

Adjuvants may optionally be added to the compositions such as colorants, abrasive granules, anti-oxidant stabilizers, thermal degradation stabilizers, light stabilizers, conductive particles, tackifiers, flow agents, film-forming polymers, bodying agents, flatting agents, inert fillers, binders, blowing agents, fungicides, bactericides, surfactants, plasticizers, rubber tougheners and other additives known to those skilled in the art. They also can be substantially unreactive, such as fillers, both inorganic and organic. These adjuvants, if present, are added in an amount effective for their intended purpose.

In some embodiments, a toughening agent may be used. The toughening agents which are useful in the present invention are polymeric compounds having both a rubbery phase and a thermoplastic phase such as: graft polymers having a polymerized, diene, rubbery core and a polyacrylate, polymethacrylate shell; graft polymers having a rubbery, polyacrylate core with a polyacrylate or polymethacrylate shell; and elastomeric particles polymerized in situ in the epoxide from free radical polymerizable monomers and a copolymerizable polymeric stabilizer.

Examples of useful toughening agents of the first type include graft copolymers having a polymerized, diene, rubbery backbone or core to which is grafted a shell of an acrylic acid ester or methacrylic acid ester, monovinyl aromatic hydrocarbon, or a mixture thereof, such as disclosed in U.S. Pat. No. 3,496,250 (Czerwinski), incorporated herein by reference. Preferable rubbery backbones comprise polymerized butadiene or a polymerized mixture of butadiene and styrene. Preferable shells comprising polymerized methacrylic acid esters are lower alkyl ($C_1$-$C_4$) substituted methacrylates. Preferable monovinyl aromatic hydrocarbons are styrene, alphamethylstyrene, vinyltoluene, vinylxylene, ethylvinylbenzene, isopropylstyrene, chlorostyrene, dichlorostyrene, and ethylchlorostyrene. It is important that the graft copolymer contain no functional groups that would poison the catalyst.

Examples of useful toughening agents of the second type are acrylate core-shell graft copolymers wherein the core or backbone is a polyacrylate polymer having a glass transition temperature below about 0° C., such as polybutyl acrylate or polyisooctyl acrylate to which is grafted a polymethacrylate polymer (shell) having a glass transition above about 25° C., such as polymethylmethacrylate.

The third class of toughening agents useful in the invention comprises elastomeric particles that have a glass transition temperature ($T_g$) below about 25° C. before mixing with the other components of the composition. These elastomeric particles are polymerized from free radical polymerizable monomers and a copolymerizable polymeric stabilizer that is soluble in the resins. The free radical polymerizable monomers are ethylenically unsaturated monomers or diisocyanates combined with coreactive difunctional hydrogen compounds such as diols, diamines, and alkanolamines.

Useful toughening agents include core/shell polymers such as methacrylate-butadiene-styrene (MBS) copolymer wherein the core is crosslinked styrene/butadiene rubber and the shell is polymethylacrylate (for example, ACRYLOID KM653 and KM680, available from Rohm and Haas, Philadelphia, PA), those having a core comprising polybutadiene and a shell comprising poly(methyl methacrylate) (for example, KANE ACE M511, M521, B11A, B22, B31, and M901 available from Kaneka Corporation, Houston, TX and CLEARSTRENGTH C223 available from ATOFINA, Philadelphia, PA), those having a polysiloxane core and a polyacrylate shell (for example, CLEARSTRENGTH S-2001 available from ATOFINA and GENIOPERL P22 available from Wacker-Chemie GmbH, Wacker Silicones, Munich, Germany), those having a polyacrylate core and a poly(methyl methacrylate) shell (for example, PARALOID EXL2330 available from Rohm and Haas and STAPHYLOID AC3355 and AC3395 available from Takeda Chemical Company, Osaka, Japan), those having an MBS core and a poly(methyl methacrylate) shell (for example, PARALOID EXL2691A, EXL2691, and EXL2655 available from Rohm and Haas) and the like and mixtures thereof. Preferred modifiers include the above-listed ACRYLOID and PARALOID modifiers and the like, and mixtures thereof.

The toughening agent is useful in an amount equal to about 1-35 parts by weight, preferably about 3-25 parts by weight, relative to 100 parts by weight of the polymerizable component of the polymerizable composition. The toughening agent adds strength to the composition after curing without reacting with the component of the polymerizable composition or interfering with curing.

In some embodiments the polymerizable composition may include one or more non-free radically polymerizable film-forming polymer. The term "film-forming organic polymer" refers to an organic polymer that will uniformly coalesce upon drying. Film-forming polymers suitable for use in the compositions are generally thermoplastic organic polymers.

Examples of suitable polymers include: polyesters, for example, polyethylene terephthalate or polycaprolactone; copolyesters, for example, polyethylene terephthalate isophthalate; polyamides, for example, polyhexamethylene adipamide; vinyl polymers, for example, poly(vinyl acetate/methyl acrylate), poly(vinylidene chloride/vinyl acetate); polyolefins, for example, polystyrene and copolymers of styrene with acrylate(s) such as, for example, poly(styrene-co-butyl acrylate); polydienes, for example, poly(butadiene/styrene); acrylic polymers, for example, poly(methyl methacrylate-co-ethyl acrylate), poly(methyl acrylate-co-acrylic acid); polyurethanes, for example, reaction products of aliphatic, cycloaliphatic or aromatic diisocyanates with polyester glycols or polyether glycols; and cellulosic derivatives, for example, cellulose ethers such as ethyl cellulose and cellulose esters such as cellulose acetate/butyrate. Combinations of film-forming polymers may also be used. Methods and materials for preparing aqueous emulsions or latexes of such polymers are well known, and many are widely available from commercial sources.

In some embodiments the crosslinkable composition may include filler. In some embodiments the total amount of filler is at most 50 wt. %, preferably at most 30 wt. %, and more preferably at most 10 wt. % filler. Fillers may be selected from one or more of a wide variety of materials, as known in the art, and include organic and inorganic filler. Inorganic filler particles include silica, submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911(Kangas et al.), and U.S. Pat. No. 7,649,029 (Kolb et al.).

In some embodiments the filler may be surface modified. A variety of conventional methods are available for modifying the surface of nanoparticles including, e.g., adding a surface-modifying agent to nanoparticles (e.g., in the form of a powder or a colloidal dispersion) and allowing the surface-modifying agent to react with the nanoparticles. Other useful surface-modification processes are described in, e.g., U.S. Pat. No. 2,801,185 (Iler), U.S. Pat. No. 4,522,958 (Das et al.) U.S. Pat. No. 6,586,483 (Kolb et al.), each incorporated herein by reference.

Surface-modifying groups may be derived from surface-modifying agents. Schematically, surface-modifying agents can be represented by the formula X—Y, where the X group is capable of attaching to the surface of the particle (i.e., the silanol groups of a silica particle) and the Y group is a reactive or non-reactive functional group. A non-functional group does not react with other components in the system (e.g. the substrate). Non-reactive functional groups can be selected to render the particle relatively more polar, relatively less polar or relatively non-polar. In some embodiments the non-reactive functional group "Y" is a hydrophilic group such as an acid group (including carboxylate, sulfonate and phosphonate groups), ammonium group or poly(oxyethylene) group, or hydroxyl group. In other embodiments, "Y" may be a reactive functional group such as an ethylenically unsaturated polymerizable group, including vinyl, allyl, vinyloxy, allyloxy, and (meth)acryloyl, that may be free-radically polymerized with the polymerizable resin or monomers.

Such optional surface-modifying agents may be used in amounts such that 0 to 100%, generally 1 to 90% (if present) of the surface functional groups (Si-OH groups) of the silica nanoparticles are functionalized. The number of functional groups is experimentally determined where quantities of nanoparticles are reacted with an excess of surface modifying agent so that all available reactive sites are functionalized with a surface modifying agent. Lower percentages of functionalization may then be calculated from the result. Generally, the amount of surface modifying agent is used in amount sufficient to provide up to twice the equal weight of surface modifying agent relative to the weight of inorganic nanoparticles. When used, the weight ratio of surface modifying agent to inorganic nanoparticles is preferably 2:1 to 1:10. If surface-modified silica nanoparticles are desired, it is preferred to modify the nanoparticles prior to incorporation into the coating composition.

The present polymerizable compositions are also useful in the preparation of hardcoats and structural or semi-structural adhesives. The term "hardcoat" or "hardcoat layer" means a layer or coating that is located on the external surface of an object, where the layer or coating has been designed to at least protect the object from abrasion.

The present disclosure provides hardcoat compositions comprising the redox initiator system and a multifunctional (meth)acrylate monomer comprising two (preferably three) or more (meth)acrylate groups, and/or a multifunctional (meth)acrylate oligomer and optionally a (meth)acrylate-functional diluent.

Useful multifunctional (meth)acrylate monomers comprise three or more (meth)acrylate groups. Multifunctional (meth)acrylate monomers are useful in the practice of the present invention because they add abrasion resistance to the hard coat layer. Preferred multifunctional (meth)acrylate monomers comprising three or more (meth)acrylate groups include trimethylol propane tri(meth)acrylate (TMPTA), pentaerythritol tri(meth)acrylate, pentaerythritol tetra(meth)acrylate, dipentaerithritol tri(meth)acrylate (Sartomer 355), dipentaerythritol penta(meth)acrylate (Sartomer 399), dipentaerythritol hydroxy penta(meth)acrylate (DPHPA), glyceryl propoxy tri(meth)acrylate, trimethylolpropane tri (meth)acrylate, and mixtures thereof. Another useful radiation-curable component of the present invention is the class of multifunctional (meth)acrylate oligomers, having two or more (meth)acrylate groups, and having an average molecular weight ($M_w$) in the range from about 400 to 2000.

Useful multifunctional (meth)acrylate oligomers include polyester (meth)acrylates, polyurethane (meth)acrylates, and (meth)acrylated epoxy (meth)acrylates. (Meth)acrylated epoxy (meth)acrylates and polyester(meth)acrylates are most preferred because they tend to have a relatively low viscosity and therefore allow a more uniform layer to be applied by the spin coating method. Specifically, preferred multifunctional (meth)acrylate oligomers include those commercially available from UCB Radcure, Inc. of Smyrna, Georgia and sold under the trade name EBECRYL (Eb): Eb40 (tetrafunctional acrylated polyester oligomer), ENO (polyester tetra-functional (meth)acrylate oligomer), Eb81 (multifunctional (meth)acrylated polyester oligomer), Eb600 (bisphenol A epoxy di(meth)acrylate), Eb605 (bisphenol A epoxy di(meth)acrylate diluted with 25% tripropylene glycol di(meth)acrylate), Eb639 (novolac polyester oligomer), Eb2047 (trifunctional acrylated polyester oligomer), Eb3500 (di-functional Bisphenol-A oligomer acrylate), Eb3604 (multi-functional polyester oligomer acrylate), Eb6602 (trifunctional aromatic urethane acrylate oligomer), Eb8301 (hexafunctional aliphatic urethane acrylate), EbW2 (difunctional aliphatic urethane acrylate oligomer), and mixtures thereof. Of these, the most preferred are, Eb 600, Eb605, Eb80, and Eb81.

Molecular weight may be controlled through the use of chain transfer agents and chain retarding agents, including mercaptans, disulfides, triethyl silane, carbon tetrabromide, carbon tetrachloride, alpha-methyl styrene and others such as are known in the art.

In some embodiments, the multifunctional (meth)acrylate oligomers may comprise a reactive oligomer having pendent polymerizable groups comprising:

a) greater than 50 parts by weight, preferably greater than 75 parts by weight, most preferably greater than 80 parts by weight of (meth)acrylate ester monomer units;

b) 1 to 10 parts by weight, preferably 1 to 5 parts by weight, most preferably 1 to 3 parts by weight, of monomer units having a pendent, free-radically polymerizable functional group, c) 0 to 20 parts by weight of other polar monomer units, wherein the sum of the monomer units is 100 parts by weight.

The reactive oligomer may be represented by the formula:

   II where $[M^{Unsatd}]$ represents monomer units having a pendent, free-radically polymerizable functional groups and subscript "o" is the parts be weight thereof;

$[W^{ester}]$ represents (meth)acrylate ester monomer units and subscript "p" represents the parts by weight thereof; and $[W^{polar}]$ represents polar monomer units and subscript "q" represents the parts by weight thereof.

The reactive oligomers (II) of the composition comprise one or more pendent groups that include free-radically polymerizable unsaturation, including (meth)acryloyl, (meth)acryloxy, propargyl, vinyl, allyl, acetylenyl and (meth)acrylamide. That is, the monomer units $[M^{Unatd}]$ contain such polymerizable groups.

An indirect method of incorporating pendent polymerizable unsaturated groups into the oligomers is to include a reactive functional group among the monomer units of the precursor oligomer that may be further functionalized with an ethylenically unsaturated compound having a functional group that is co-reactive with the functional group of the precursor oligomer.

Useful reactive functional groups include, but are not limited to, hydroxyl, amino, oxazolonyl, oxazolinyl, acetoacetyl, azlactonyl, carboxyl, isocyanato, epoxy, aziridinyl, acyl halide, and cyclic anhydride groups. Preferred among these are carboxyl, hydroxyl, amino, azlactonyl and aziridinyl groups. These pendent reactive functional groups are reacted with unsaturated compounds that comprise functional groups that are co-reactive with the reactive pendent functional group. When the two functional groups react, an oligomer with pendent unsaturation results. In some applications, it may be desirable to use less than a stoichiometric equivalent of unsaturated compounds that comprise co-reactive functional groups, so that some of the pendent functional groups on the oligomer(s) remain unreacted. Specifically, the reactive oligomers of Formula III may be prepared from a precursor oligomer having monomer units of the formula $[M^{FG}]$, having reactive functional groups that may be functionalized to provide the reactive oligomer of Formula II.

Using the "indirect method" of incorporating the pendent, free-radically polymerizable functional groups, useful reactive functional groups include hydroxyl, secondary amino, oxazolinyl, oxazolonyl, acetyl, acetonyl, carboxyl, isocyanato, epoxy, aziridinyl, acyl halide, vinyloxy, and cyclic anhydride groups. Where the pendent reactive functional group is an isocyanato functional group, the co-reactive functional group preferably comprises a secondary amino or hydroxyl group. Where the pendent reactive functional group comprises a hydroxyl group, the co-reactive functional group preferably comprises a carboxyl, ester, acyl halide, isocyanato, epoxy, anhydride, azlactonyl or oxazolinyl group. Where the pendent reactive functional group comprises a carboxyl group, the co-reactive functional group preferably comprises a hydroxyl, amino, epoxy, isocyanate, or oxazolinyl group. Most generally, the reaction is between a nucleophile and electrophilic functional groups.

Preferred ethylenically unsaturated compounds that may be used to functionalize the precursor oligomer have the general formula:

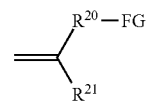   III wherein $R^{21}$ is hydrogen, a $C_1$ to $C_4$ alkyl group, or a phenyl group, preferably hydrogen or a methyl group; $R^{20}$ is a single bond or a divalent linking group that joins an ethylenically unsaturated group to a co-reactive functional group "FG" and preferably contains up to 34, preferably up to 18, more preferably up to 10, carbon and, optionally, oxygen and nitrogen atoms and, when $R^{20}$ is not a single bond, is preferably selected from

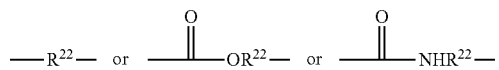

in which $R^{22}$ is an alkylene group having 1 to 6 carbon atoms, a 5- or 6-membered cycloalkylene group having 5 to 10 carbon atoms, or an alkylene-oxyalkylene in which each alkylene includes 1 to 6 carbon atoms or is a divalent aromatic group having 6 to 16 carbon atoms; and FG is a co-reactive functional group, that is capable of reacting with a pendent reactive functional group of the oligomer for the incorporation of a free-radically polymerizable functional group.

Representative examples of useful compounds of Formula III having co-reactive functional groups include hydroxyalkyl (meth)acrylates such as 2-hydroxyethyl (meth)acrylate, 3-hydroxypropyl (meth)acrylate, 2, 3-dihydroxypropyl (meth)acrylate, 4-hydroxybutyl (meth)acrylate and 2-(2-hydroxyethoxy)ethyl (meth)acrylate; aminoalkyl (meth)acrylates such as 3-aminopropyl (meth)acrylate and 4-aminostyrene; oxazolinyl compounds such as 2-ethenyl-1,3-oxazolin-5-one, 2-vinyl-4,4-dimethyl-1,3-oxazolin-5-one, 2-isopropenyl-4,4-dimethyl-1,3-oxazolin-5-one and 2-propenyl-4,4-dimethyl-1,3-oxazolin-5-one; carboxy-substituted compounds such as (meth)acrylic acid and 4-carboxybenzyl (meth)acrylate; isocyanato-substituted compounds such as isocyanatoethyl (meth)acrylate and 4-isocyanatocyclohexyl (meth)acrylate; epoxy-substituted compounds such as glycidyl (meth)acrylate; aziridinyl-substituted compounds such as N-acryloylaziridine and 1-(2-propenyl)-aziridine; and acryloyl halides such as (meth)acryloyl chloride.

The reactive oligomer may be redox polymerized per se, or with a multifunctional acrylate, such as hexanediol di(meth)acrylate. The reactive oligomer having pendent polymerizable groups may be prepared as described in U.S. Pat. No. 7,598,298 (Lewandowski et al.), U.S. Pat. No. 7,342,047 (Lewandowski et al.) and U.S. Pat. No. 7,074,839 (Fansler et al.), each incorporated herein by reference.

The polymerizable reactive oligomer component may further comprise a diluent monomer. The (meth)acrylate-functional diluents, also referred to herein as "reactive diluents", are relatively low molecular weight mono- or di-functional, non-aromatic, (meth)acrylate monomers. These relatively low molecular weight reactive diluents are advantageously of a relatively low viscosity, e.g., less than about 30 centipoise (cps) at 25° C. Di-functional, non-aromatic (meth)acrylates are generally preferred over mono-functional non-aromatic (meth)acrylates because di-functional non-aromatic (meth)acrylates allow for quicker cure time. Preferred reactive diluents include 1,6-hexanediol di(meth)acrylate (HDDA from UCB Radcure, Inc. of Smyrna, Georgia), tripropylene glycol di(meth)acrylate, isobornyl (meth)acrylate (1130A, Radcure), 2(2-ethoxyethoxy) ethyl (meth)acrylate (sold under the trade name Sartomer 256 from SARTOMER Company, Inc. of Exton, Pennsylvania), n-vinyl formamide (Sartomer 497), tetrahydrofurfuryl (meth)acrylate (Sartomer 285), polyethylene glycol di(meth)acrylate (Sartomer 344), tripropylene glycol di(meth)acrylate (Radcure), neopentyl glycol dialkoxy di(meth)acrylate, polyethyleneglycol di(meth)acrylate, and mixtures thereof.

In some embodiments the polymerizable composition may comprise: 20-80 parts by weight of multifunctional (meth)acrylate monomers and/or multifunctional (meth)acrylate reactive oligomers,
0 to parts by weight range of (meth)acrylate diluent,
20 to 75 wt. % of silica (per se, whether or not functionalized), and
from about 0.1 weight percent to about 5.0 weight percent of the redox initiator system, based on the 100 parts by weight of the polymerizable components of the polymerizable composition.

In some embodiments, the polymerizable composition provides a structural and semi-structural adhesive composition in which the partially cured composition may be disposed between two substrates (or adherends), and subsequently fully cured to effect a structural or semi-structural bond between the substrates. "Semi-structural adhesives" are those cured adhesives that have an overlap shear strength of at least about 0.5 MPa, more preferably at least about 1.0 MPa, and most preferably at least about 1.5 MPa. Those cured adhesives having particularly high overlap shear strength, however, are referred to as structural adhesives. "Structural adhesives" are those cured adhesives that have an overlap shear strength of at least about 3.5 MPa, more preferably at least about 5 MPa, and most preferably at least about 7 MPa.

In some embodiments the present disclosure provides an adhesive composition comprising the redox initiator system and a) a first reactive oligomer comprising (meth)acrylate ester monomer units, hydroxyl-functional monomer units, and monomer units having polymerizable groups; b) a second component comprising $C_2$-$C_4$ alkylene oxide repeat units and polymerizable terminal groups, and c) a diluent monomer component.

The first component reactive oligomer is of the general formula:

$\sim[M^{Ester}]_a\text{-}[M^{OH}]_b\text{-}[M^{Polar}]_c\text{-}[M^{Silyl}]_e\text{-}[M^{Poly}]_d\sim$, where
-[$M^{Ester}$]- represents interpolymerized (meth)acrylate ester monomer units and subscript a is greater than 50 parts by weight;
-[$M^{OH}$]- represents interpolymerized (meth)acryloyl monomer units having a pendent hydroxy groups where subscript b represents 0 to 20 parts by weight.
[$M^{Polar}$] represent optional polar monomer units, where subscript c is 0-20, preferably 1-10 parts by weight,
[$M^{Silyl}$] represent silyl functional monomer units, where subscript e is 0 to 10, preferably 1-5 parts by weight; and
[$M^{Poly}$] represents monomer units comprising polymerizable groups silane-functional monomer units and subscript d represents 1-10 parts by weight. The sum of subscripts a to e being 100 parts by weight. The tilde represents the continuing polymr chain. Such reactive oligomers are further described in Applicant's copending US 2015/0284601 (Yurt et al., incorporated herein by reference) and in WO 2014/078115 (Behling et al.). As taught in Yurt '601, the oligomer is functionalized with the polymerizable groups ($M^{Poly}$ units) by functionalization of the pendent hydroxy groups of the $M^{OH}$ monomer. The second component of the Yurt '601 composition is at comprising $C_2$-$C_4$ alkylene oxide units and 1 to 3 terminal polymerizable groups, such as (meth)acrylate groups.

In some embodiments the amount of silica, including the silica modified with conventional surface modifying agents and unmodified silica is 20-75 wt. %, preferably 50-70 wt. %.

Filler components include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), U.S. Pat. No. 7,156,911(Kangas et al.), and U.S. Pat. No. 7,649,029 (Kolb et al.).

The present polymerization may be conducted in bulk, or in a solvent. Solvents, preferably organic, can be used to assist in the dissolution of the initiator and initiator system in the polymerizable monomers, and as a processing aid. Preferably, such solvents are not reactive with components. It may be advantageous to prepare a concentrated solution of the transition metal complex in a small amount of solvent to simplify the preparation of the polymerizable composition.

Suitable solvents include ethers such as diethyl ether, ethyl propyl ether, dipropyl ether, methyl t-butyl ether, di-t-butyl ether, glyme (dimethoxyethane), diglyme, diethylene glycol dimethyl ether; cyclic ethers such as tetrahydrofuran and dioxane; alkanes; cycloalkanes; aromatic hydrocarbon solvents such as benzene, toluene, o-xylene, m-xylene, p-xylene; halogenated hydrocarbon solvents; acetonitrile; lactones such as butyrolactone, and valerolactones; ketones such as acetone, methyl ethyl ketone, methyl isobutyl ketone, cyclopentanone, and cyclohexanone; sulfones such as tetramethylene sulfone, 3-methylsulfolane, 2,4-dimethylsulfolane, butadiene sulfone, methyl sulfone, ethyl sulfone, propyl sulfone, butyl sulfone, methyl vinyl sulfone, 2-(methylsulfonyl) ethanol, and 2,2'-sulfonyldiethanol; sulfoxides such as dimethyl sulfoxide; cyclic carbonates such as propylene carbonate, ethylene carbonate and vinylene carbonate; carboxylic acid esters such as ethyl acetate, Methyl Cellosolve™ and methyl formate; and other solvents such as methylene chloride, nitromethane, acetonitrile, glycol sulfite and 1,2-dimethoxyethane (glyme), mixtures of such solvents, and supercritical solvents (such as $CO_2$). The present polymerization may also be conducted in accordance with known suspension, emulsion and precipitation polymerization processes.

Preferably, the monomer(s) and components of the redox initiator system are selected such that the rate of initiation is not less than 1,000 times (preferably not less than 100 times) slower than the rate of propagation and/or transfer of the generated radical group to the polymer radical. In the present application, "propagation" refers to the reaction of a polymer radical with a monomer to form a polymer-monomer adduct radicals.

Polymerizing may be conducted at a temperature of from −78 to 200° C., preferably from 0 to 160° C. and most preferably from 20 to 100° C. The reaction should be conducted for a length of time sufficient to convert at least 10% (preferably at least 50%, more preferably at least 75% and most preferably at least 90%) of the monomer to polymer. Typically, the reaction time for complete cure will be from several minutes to 5 days, preferably from 30 minutes to 3 days, and most preferably from 1 to 24 hours.

Preferably the polymerizable composition comprises a "two-part" system in which the transition metal complex is in the first mixture, and the oxidizing agent, the photolabile reducing agent and any filler is generally in a first mixture. The polymerizable monomer may be part of the first and/or second mixture and is preferably in the first mixture. The two parts are combined, optionally coated on a substrate, and the redox reaction initiated by exposure to actinic radiation. In another embodiment, the polymerizable composition comprises a "two-part" system in which the transition metal complex, photolabile reducing agent and polymerizable monomer component is in the first mixture, and the oxidant is in the second mixture.

The polymerizable composition and the redox initiator system may be combined and irradiated with activating UV radiation to cleave or fragment the photolabile transition metal complex, initiate the redox cycle and polymerize the polymerizable component(s). UV light sources can be of two types: 1) relatively low light intensity sources such as backlights which provide generally 10 mW/cm² or less (as measured in accordance with procedures approved by the United States National Institute of Standards and Technology as, for example, with a Uvimap™ UM 365 L-S radiometer manufactured by Electronic Instrumentation & Technology, Inc., in Sterling, VA) over a wavelength range of 280 to 400 nanometers and 2) relatively high light intensity sources such as medium pressure mercury lamps which provide intensities generally greater than 10 mW/cm², preferably between 15 and 450 mW/cm². Where actinic radiation is used to fully or partially polymerize the polymerizable composition, high intensities and short exposure times are preferred. For example, an intensity of 600 mW/cm² and an exposure time of about 1 second may be used successfully. Intensities can range from about 0.1 to about 150 mW/cm², preferably from about 0.5 to about 100 mW/cm², and more preferably from about 0.5 to about 50 mW/cm². UV LEDs may also be used, such as a Clearstone UV LED lamp (Clearstone Technologies Inc. Hopkins MN 385 nm).

The above-described compositions are coated on a substrate using conventional coating techniques modified as appropriate to the particular substrate. For example, these compositions can be applied to a variety of solid substrates by methods such as roller coating, flow coating, dip coating, spin coating, spray coating, knife coating, and die coating. These various methods of coating allow the compositions to be placed on the substrate at variable thicknesses thus allowing a wider range of use of the compositions.

The polymerizable compositions may be coated upon a variety of flexible and inflexible substrates using conventional coating techniques to produce coated articles. Flexible substrates are defined herein as any material which is conventionally utilized as a tape backing or may be of any other flexible material. Examples include, but are not limited to, plastic films such as polypropylene, polyethylene, polyvinyl chloride, polyester (polyethylene terephthalate), polycarbonate, polymethyl(meth)acrylate (PMMA), cellulose acetate, cellulose triacetate, and ethyl cellulose. Foam backings may be used.

In some preferred embodiments, the substrate may be chosen so as to be transparent to the UV radiation used to initiate the redox cycle. The coated article may then be initiated through the thickness of the transparent substrate.

In some embodiments, the substrate is a release liner to form an adhesive article of the construction substrate/adhesive layer/release liner or release liner/adhesive/release liner. The adhesive layer may be cured, uncured or partially cured. Release liners typically have low affinity for the curable composition. Exemplary release liners can be prepared from paper (e.g., Kraft paper) or other types of polymeric material. Some release liners are coated with an outer layer of a release agent such as a silicone-containing material or a fluorocarbon-containing material. Release coating can be applied by solvent or solvent-free methods

EXAMPLES

Materials

The materials with their sources were as listed in Table 1. Unless stated otherwise, all other reagents were obtained, or are available from fine chemical vendors such as Sigma-Aldrich Company, St. Louis, Missouri, or may be synthesized by known methods.

TABLE 1

Materials List

| Designation | Description |
|---|---|
| BF9-88 | Plasticizer obtained under the trade designation BENZOFLEX 9-88 from Eastman Chemical Company, Kingsport, TN |
| Benzyl tributyl ammonium chloride | Obtained from Alfa Aesar, Ward Hill, MA |
| $CH_2Cl_2$ | Dichloromethane ($CH_2Cl_2$) obtained from EMD Millipore Corporation, Billerica, MA |
| Copper (II) acetate monohydrate | Obtained from Alfa Aesar, Ward Hill, MA |

TABLE 1-continued

Materials List

| Designation | Description |
| --- | --- |
| CHP | Cumene hydroperoxide; technical grade, 80%, obtained from Alfa Aesar, Ward Hill, MA |
| 1,3-Dimethylbarbituric acid | Obtained from Alfa Aesar, Ward Hill, MA |
| Ethyl acetate | Obtained from VWR International, Radnor, PA |
| HEMA | 2-Hydroxyethyl methacrylate obtained from TCI America, Portland, OR |
| 2-Nitrobenzyl alcohol | Obtained from Alfa Aesar, Ward Hill, MA |
| $POCl_3$ | Phosphorus (V) oxychloride obtained from Alfa Aesar, Ward Hill, MA |
| Propylene carbonate | Obtained from Alfa Aesar, Ward Hill, MA |
| SP200 | Adhesion monomers obtained under the trade designation SIPOMER PAM-200 from Solvay, Houston, TX |
| TEGDMA | Triethylene glycol dimethacrylate obtained from Sigma Aldrich, St. Louis, MO |
| EtOAc | Ethyl acetate obtained from Sigma Aldrich, St. Louis, MO |
| Acetic acid (AcOH) | Glacial acetic acid obtained from EMD Millipore Corp., Billerica, MA |
| Acetic anhydride | Obtained from EMD Millipore Corp., Billerica, MA |
| Acetone | Obtained from Avantor Performance Materials, Inc., Center Valley, PA |
| Acm | Acrylamide from Zibo Xinye Chemical Company, Zibo, China |
| BA | n-Butyl acrylate from BASF Corp. |
| Benzaldehyde | Obtained from Sigma Aldrich, Inc., St. Louis, MO |
| CHA | Cyclohexyl acrylate from TCI America, Portland, Oregon |
| Chloroform ($CHCl_3$) | Obtained from EMD Millipore Corp., Billerica, MA |
| CN1964 | Urethane dimethacrylate oligomer from Sartomer Co., Exton, Pennsylvania |
| $Cu(naph)_2$ in mineral spirits | Copper (II) naphthenate in mineral spirits (6% Cu) obtained from Pfaltz & Bauer, Waterbury, CT |
| 1,3-Dimethylurea | Obtained from Oakwood Chemicals, Estill, SC |
| 2EHA | 2-ethylhexyl acrylate from BASF Corp., Florham Park, New Jersey |
| Ethanol (EtOH) | Anhydrous Ethanol, obtained from EMD Millipore Corp., Billerica, MA |
| Ethyl-4-chloroacetoacetate | Obtained from Alfa Aesar, Heysham, England |
| HPA | Hydroxypropyl acrylate (mixture of isomers) from BASF Corp. |
| IEM | 2-isocyanatoethyl methacrylate from TCI America |
| MEK | Methyl ethyl ketone from Avantor Performance Materials, Center Valley, PA |
| Methanesulfonic acid | Obtained from Alfa Aesar, Ward Hill, MA |
| 3-Methoxy phenol | Obtained from TCI Chemicals, Tokyo, Japan |
| Phenylmalonic acid | Obtained from Sigma-Aldrich, St. Louis, MO |
| RL1 | a siliconized polyester film release liner |
| Sodium borohydride ($NaBH_4$) | Obtained from Aldrich Chemical Company, Inc., Milwaukee, WI |
| TBEC | Tert-Butylperoxy 2-ethylhexyl carbonate obtained from Sigma Aldrich, St. Louis, MO |
| TDDM | Tertiary dodecyl mercaptan from Sartomer Co. |
| THFMA | Tetrahydrofuryl methacrylate obtained as SR203 from Sartomer, Warrington, PA |
| VAZO-52 | 2,2'-azobis(2,4-dimethylpentatenitrile), thermal radical initiator obtained as VAZO 52 from E. I. du Pont de Nemours & Co., Wilmington, Delaware |

Preparative Example 1 (PE 1)

Synthesis of 2-nitrobenzyl blocked 1,3-dimethyl barbituric acid

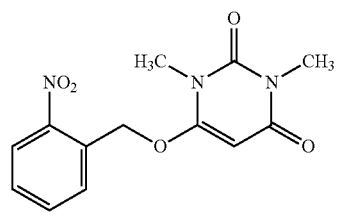 [SMILES: Cn1c(OCc2ccccc2[N+](=O)[O-])cc(=O)n(C)c1=O]

A suspension of 1,3-dimethylbarbituric acid (7.80 grams (g), 50.0 millimole (mmol)) in $POCl_3$ (60.0 milliliters (mL), 660 mmol) was cooled in an ice water bath, and deionized water (2.5 mL, 140 mmol) was added dropwise. The resultant cloudy mixture was heated at reflux for 1 hour, during which time it became clear and pale yellow. The excess $POCl_3$ was removed under reduced pressure, and the yellow residue was dissolved in $CH_2Cl_2$ and washed sequentially with saturated aqueous $NaHCO_3$, water, and saturated aqueous sodium chloride. The organic layer was then dried over $MgSO_4$, filtered, and concentrated to a pale yellow solid. Purification via suction filter column ($SiO_2$, EtOAc eluent) affords a white crystalline solid (7.70 grams). A portion of this material (3.49 g) was dissolved in $CH_2Cl_2$ (50 mL) and added to a mixture of 2-nitrobenzyl alcohol (4.59 g, 30.0 mmol), benzyl tributyl ammonium chloride (0.62 g, 2.0 mmol) and NaOH (4.0 g, 100 mmol) in deionized H$_2$O (80 mL). The resultant biphasic mixture was allowed to stir vigorously overnight at ambient temperature. The organic layer was then washed sequentially with water and saturated aqueous sodium chloride, then dried over MgSO$_4$, filtered, and concentrated to afford a yellow solid. Purification via suction filter column (SiO$_2$, EtOAc eluent) affords the product as a pale yellow solid (4.60 grams, 70% yield for the two steps). The $^1$H NMR spectrum was consistent with the desired product.

The examples below consist of a 10:1 mixture of a base resin and an accelerator according to Tables 2 and 3, respectively. The base resins consist of an acrylic monomer, transition metal salt, and optionally an ammonium halide salt. The base resins were prepared by adding all components into a DAC mixing cup (FlackTek Inc., Landrum, SC) and mixing until homogeneous.

TABLE 2

Base Formulations 1 to 6 (B1 to B6)

| Component | B1 | B2 | B3 | B4 | B5 | B6 |
| --- | --- | --- | --- | --- | --- | --- |
| HEMA | 9.45 g | 9.45 g | 9.45 g | 9.93 g | 9.93 g | 9.93 g |
| Ammonium chloride solution* | 0.48 g | 0.48 g | 0.48 g | — | — | — |
| Copper acetate | 0.07 g** | 0.07 g*** | 0.07 g**** | 0.07 g** | 0.07 g*** | 0.07 g**** |
| Total | 10.00 g | 10.00 g | 10.00 g | 10.00 g | 10.00 g | 10.00 g |

*Ammonium chloride solution is 5 wt % benzyltributyl ammonium chloride in HEMA.
**Copper acetate is 4 wt % Cu(II) acetate monohydrate in HEMA.
***Copper acetate is 4 wt % Cu(II) acetate monohydrate in 7:1 TEGDMA/SP200.
****Copper acetate is 4 wt % Cu(II) acetate monohydrate in 3:1 TEGDMA/SP200.

The accelerator consists of a diluent, an initiator molecule, and a peroxide (Table 3). The accelerator was prepared by adding all components into a small glass vial equipped with stirbar, and stirring to ensure homogeneity.

TABLE 3

Accelerator Formulation 1 (A1)

| Component | A1 |
| --- | --- |
| BF9-88 | 2.18 g |
| Initiator solution* | 0.75 g |
| CHP** | 0.07 g |
| Total | 3.00 g |

*Initiator solution comprising 10 wt % of PE 1 in propylene carbonate.
**CHP is technical grade cumene hydroperoxide.

Table 4 below demonstrates the use of PE 1 as an initiator compound, Examples 1-6 (EX 1-6). Formulations were prepared by addition of 1.50 g applicable base resin (Table 2) and 0.15 g accelerator (Table 3) into a small glass vial and shaking for approximately 30 seconds to ensure homogeneity. Immediately afterwards, 1 drop of the mixed formulation was placed on a glass microscope slide (75×38×1.0 mm, from Fisher Scientific, Pittsburgh, PA) and covered with a microscope cover glass (22×22 mm, from Fisher Scientific, Pittsburgh, PA). When applicable, samples were irradiated using an LX-400 instrument (Lumen Dynamics, Mississauga, Ontario, Canada) equipped with a 365 nm LED lamp, holding the lamp within 1 centimeter (cm) of the surface of the cover glass for 30 seconds. Cure time was defined as the point at which the cover glass could no longer be moved by hand. Without irradiation, all mixed two-part formulations without ammonium chloride were stable for greater than 420 minutes. Upon incorporation of ammonium chloride, stability of these mixed two-part formulations decreased, with curing taking place within 240 minutes. For EX 1-6, the brief irradiation was highly effective at triggering the redox cure. The fastest curing was observed upon irradiation of formulations containing ammonium chloride salt.

TABLE 4

Examples 1-6 (EX 1-6)

| | Initiator | Base resin, g | Accelerator, g | Ammonium chloride | Cure time, no irradiation | Cure time, 30 seconds irradiation |
| --- | --- | --- | --- | --- | --- | --- |
| EX 1 | PE 1 | B1, 1.5 | A1, 0.15 | Yes | 40 minutes | 8 minutes |
| EX 2 | PE 1 | B4, 1.5 | A1, 0.15 | No | >420 minutes | 50 minutes |
| EX 3 | PE 1 | B2, 1.5 | A1, 0.15 | Yes | 90 minutes | 25 minutes |
| EX 4 | PE 1 | B5, 1.5 | A1, 0.15 | No | >420 minutes | 120 minutes |
| EX 5 | PE 1 | B3, 1.5 | A1, 0.15 | Yes | 240 minutes | 40 minutes |
| EX 6 | PE 1 | B6, 1.5 | A1, 0.15 | No | >420 minutes | 220 minutes |

Preparative Example 2 (PE 2)

Synthesis of 2-nitrobenzyl-blocked 5-phenyl-1,3-dimethylbarbituric acid (b-PhDMBA)

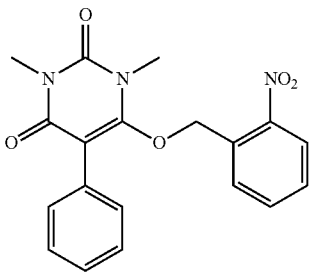 [SMILES: Cn1c(OCc2ccccc2[N+](=O)[O-])c(-c2ccccc2)c(=O)n(C)c1=O]

To a solution of 1,3-dimethylurea (2.66 grams, 30.0 mmol) and phenylmalonic acid (5.40 grams, 30.0 mmol) in CHCl$_3$ (70 mL) was added AcOH (5.5 mL, 96.0 mmol). The resultant reaction mixture was heated at 50° C. Acetic anhydride (11.3 mL, 120.0 mmol) and trifluoracetic acid (0.5 mL, 6.6 mmol) were added, and the reaction mixture was then heated at reflux while stirring overnight. The following morning, the volatile components were removed under reduced pressure, and the residue was added to water (100 mL). After stirring for 2 hours, the solid that formed was collected via filtration, washing with additional water. The solid was then dissolved in CH$_2$Cl$_2$ and washed with saturated aqueous (sat. aq.) NaCl. The organic layer was dried over MgSO$_4$, filtered, and concentrated to afford 1,3-dimethyl-5-phenylbarbituric acid (4.20 grams, 60% yield) as a white solid.

The 1,3-Dimethyl-5-phenylbarbituric acid (4.20 grams, 18.08 mmol) was dissolved in POCl$_3$ (30 mL). Water (1.0 mL) was added dropwise to the mixture, resulting in a significant exotherm. Once the exotherm had subsided, the mixture was heated at reflux for 4 hours. The majority of the POCl$_3$ was then removed under reduced pressure, and cold water was added to the residue. The mixture was extracted with CH$_2$Cl$_2$ (3×75 mL). The combined organic layers were washed sequentially with sat. aq. NaHCO$_3$, water, and sat. aq. NaCl, then dried over MgSO$_4$, filtered, and concentrated to provide an orange oil. Purification of this material via suction filter column (SiO$_2$, 3:1 hexane/EtOAc eluent) affords 1,3-dimethyl-5-phenyl-6-chlorouracil (4.30 grams, 95% yield) was a white solid.

Benzyl tri-n-butylammonium chloride (0.54 grams, 1.7 mmol) and 2-nitrobenzyl alcohol (3.94 grams, 25.7 mmol) were added to a solution of NaOH (3.43 grams, 85.8 mmol) in H$_2$O (80 mL). A solution of the 1,3-dimethyl-5-phenyl-6-chlorouracil (4.30 grams, 17.15 mmol) in CH$_2$Cl$_2$ (50 mL) was then added. The resultant biphasic mixture was allowed to stir vigorously overnight at room temperature. The following morning, the aqueous layer was adjusted to pH ~6, then extracted with CH$_2$Cl$_2$ (3×75 mL). The combined organic layers were then washed sequentially with H$_2$O and sat. aq. NaCl, then dried over MgSO$_4$, filtered, and concentrated to an orange oil. Purification of this material via suction filter column (SiO$_2$, 1:1 hexane/EtOAc eluent) affords the product (3.14 grams, 50% yield) as a white solid.

Preparative Example 3 (PE 3)

Synthesis of 2-nitrobenzyl-blocked 5-Benzyl-1,3-dimethylbarbituric acid (b-BnDMBA)

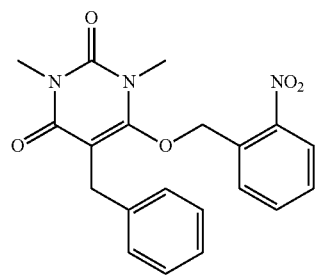 [SMILES: Cn1c(OCc2ccccc2[N+](=O)[O-])c(Cc2ccccc2)c(=O)n(C)c1=O]

To a solution of 1,3-dimethylbarbituric acid (3.90 grams, 25.0 mmol) in 100 mL hot H$_2$O was added a solution of benzaldehyde (2.65 grams, 25.0 mmol) in EtOH (20 mL). The resultant mixture was stirred vigorously while heating at reflux. After 5 hours, the mixture was allowed to cool to room temperature, and the precipitate was collected via filtration, washing with additional water. After drying overnight, this provided 5-benzylidene-1,3-dimethylpyrimidine-2,4,6-trione (5.90 grams, 97% yield) as a pale yellow solid.

The 5-benzylidene-1,3-dimethylpyrimidine-2,4,6-trione (5.90 grams, 24.15 mmol) was added to EtOH (70 mL), and NaBH4 (0.91 grams, 24.15 mmol) was added portionwise over several minutes. After 2 hours, the majority of the EtOH was removed under reduced pressure, and the residue was quenched with 100 mL of aq. IN HCl. This mixture was extracted with EtOAc (3×75 ml), and the combined organic layers were washed with sat. aq. NaCl, dried over MgSO$_4$, filtered, and concentrated to afford 5-benzyl-1,3-dimethylbarbituric acid (5.83 grams, 98% yield) as a white crystalline solid.

1,3-Dimethyl-5-benzylbarbituric acid (7.39 grams, 30.0 mmol) was dissolved in POCl$_3$ (41.4 grams, 270 mmol). Water (1.35 mL) was added dropwise to the mixture, resulting in a significant exotherm. Once the exotherm had subsided, the mixture was heated at reflux for 3 hours. The majority of the POCl$_3$ was then removed under reduced pressure, and cold water was added to the residue. The mixture was extracted with CH$_2$Cl$_2$ (3×75 mL). The combined organic layers were washed sequentially with sat. aq. NaHCO$_3$, water, and sat. aq. NaCl, then dried over MgSO$_4$, filtered, and concentrated to provide an orange oil. Purification of this material via suction filter column (SiO$_2$, 7:1 hexane/EtOAc eluent) affords 1,3-dimethyl-5-benzyl-6-chlorouracil (7.94 grams, quantitative yield) as an orange oil which slowly crystalizes to a solid.

Benzyl tri-n-butylammonium chloride (0.94 grams, 3.0 mmol) and 2-nitrobenzyl alcohol (6.13 grams, 40.0 mmol) were added to a solution of NaOH (6.0 grams, 150 mmol) in H$_2$O (90 mL). A solution of the 1,3-dimethyl-5-benzyl-6-chlorouracil (7.94 grams, 30.0 mmol) in CH$_2$Cl$_2$ (70 mL) was then added. The resultant biphasic mixture was allowed to stir vigorously overnight at room temperature. The following morning, the aqueous layer was adjusted to pH ~6, then extracted with CH$_2$Cl$_2$ (3×75 mL). The combined organic layers were then washed sequentially with H$_2$O and sat. aq. NaCl, then dried over MgSO$_4$, filtered, and concentrated to an orange oil. Purification of this material via suction filter column (SiO$_2$, ramp eluent from 7:1 hexane/

EtOAc to EtOAc) affords the product (4.20 grams, 37% yield) as a light peach colored solid.

Preparative Example 4 (PE 4)

Synthesis of Coumarin-Blocked 5-benzyl-1,3-dimethylbarbituric acid (Cou-BnDMBA)

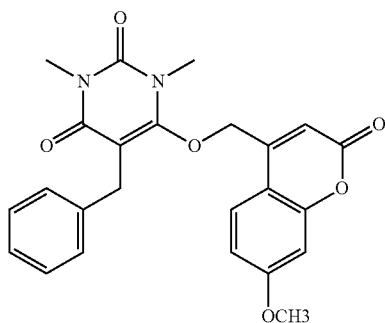 [SMILES: COc1ccc2c(COc3c(Cc4ccccc4)c(=O)n(C)c(=O)n3C)cc(=O)oc2c1]

1,3-Dimethyl-5-benzylbarbituric acid (7.39 grams, 30.0 mmol) was dissolved in POCl$_3$ (41.4 grams, 270 mmol). Water (1.35 mL) was added dropwise to the mixture, resulting in a significant exotherm. Once the exotherm had subsided, the mixture was heated at reflux for 3 hours. The majority of the POCl$_3$ was then removed under reduced pressure, and cold water was added to the residue. The mixture was extracted with CH$_2$Cl$_2$ (3×75 mL). The combined organic layers were washed sequentially with sat. aq. NaHCO$_3$, water, and sat. aq. NaCl, then dried over MgSO$_4$, filtered, and concentrated to provide an orange oil. Purification of this material via suction filter column (SiO$_2$, 7:1 hexane/EtOAc eluent) affords 1,3-dimethyl-5-benzyl-6-chlorouracil (7.94 grams, quantitative yield) as an orange oil which slowly crystalizes to a solid.

A solution of 3-methoxy phenol (3.72 grams, 30.0 mmol) and ethyl-4-chloroacetoacetate (7.41 grams, 45.0 mmol) in methanesulfonic acid (40 mL) was stirred at room temperature overnight. The following morning, ice water (200 mL) was added, and the resultant grey precipitate was collected via filtration, washing with additional H$_2$O. The collected material was dried under vacuum to afford 4-chloromethyl-7-methoxycoumarin (6.40 grams, 95% yield) as a beige solid.

To a solution of 4-chloromethyl-7-methoxycoumarin (1.35 grams, 6.00 mmol) in 1:1 DMSO/H$_2$O (30 mL) was added trifluoroacetic acid (1.0 mL). The resultant mixture was heated at reflux for 48 hours. Upon cooling, H$_2$O (100 mL) was added, and the mixture was extracted with CH$_2$Cl$_2$ (3×50 mL). The combined organic layers were washed sequentially with H$_2$O and sat. aq. NaCl, then dried over MgSO$_4$, filtered, and concentrated to a brown solid. Purification of this material via suction filter column (SiO$_2$, 97:3 CH$_2$Cl$_2$/MeOH eluent) affords 6-methoxy-1-hydroxymethyl-3-oxo-3H-benzopyran (1.11 grams, 90% yield) as a light tan solid.

Benzyl tri-n-butylammonium chloride (0.16 grams, 0.50 mmol) was added to a solution of NaOH (1.0 gram, 25.0 mmol) in H$_2$O (30 mL). A solution of 6-methoxy-1-hydroxymethyl-3-oxo-3H-benzopyran (1.03 grams, 5.00 mmol) and the 1,3-dimethyl-5-benzyl-6-chlorouracil (1.32 grams, 5.00 mmol) in CH$_2$Cl$_2$ (30 mL) was then added. The resultant biphasic mixture was allowed to stir vigorously overnight at room temperature. The following morning, the aqueous layer was adjusted to pH ~6, then extracted with CH$_2$Cl$_2$ (3×30 mL). The combined organic layers were then washed sequentially with H$_2$O and sat. aq. NaCl, then dried over MgSO$_4$, filtered, and concentrated to an orange oil. Purification of this material via suction filter column (SiO$_2$, ramp eluent from 7:1 hexane/EtOAc to EtOAc) affords the product (0.24 grams, 11% yield) as a pale yellow solid.

The examples below consist of a 10:1 mixture of a base resin and an accelerator according to Tables 5 or 6 and 7, respectively. The base resins consist of an acrylic monomer, transition metal salt, and an ammonium halide salt. The base resins were prepared by adding all components into a DAC mixing cup (FlackTek Inc., Landrum, SC) and mixing until homogeneous.

TABLE 5

| Base Formulations (THFMA-Containing) 7 to 9 (B7 to B9) | | | |
|---|---|---|---|
| Component | B7 | B8 | B9 |
| THFMA | 9.45 g | 9.45 g | 9.45 g |
| Ammonium chloride solution* | 0.48 g | 0.48 g | 0.48 g |
| Copper acetate | 0.07 g ** | 0.07 g *** | 0.07 g **** |
| Total | 10.00 g | 10.00 g | 10.00 g |

*Ammonium chloride solution is 5 wt % benzyltributyl ammonium chloride in HEMA
** Copper acetate is 4 wt % Cu(II) acetate monohydrate in 7:1 TEGDMA/SP200
*** Copper acetate is 4 wt % Cu(II) acetate monohydrate in 3:1 TEGDMA/SP200
**** Copper acetate is 4 wt % Cu(II) acetate monohydrate in 1:1 TEGDMA/SP200

TABLE 6

| Base Formulations (HEMA-Containing) 10 to 13 (B10 to B13) | | | | |
|---|---|---|---|---|
| Component | B10 | B11 | B12 | B13 |
| HEMA | 9.45 g | 9.45 g | 9.45 g | 9.45 g |
| Ammonium chloride solution* | 0.48 g | 0.48 g | 0.48 g | 0.48 g |
| Copper acetate | 0.07 g ** | 0.07 g *** | 0.07 g **** | 0.07 g ***** |
| Total | 10.00 g | 10.00 g | 10.00 g | 10.00 g |

*Ammonium chloride solution is 5 wt % benzyltributyl ammonium chloride in HEMA
** Copper acetate is 4 wt % Cu(II) acetate monohydrate in HEMA
*** Copper acetate is 4 wt % Cu(II) acetate monohydrate in 7:1 TEGDMA/SP200
**** Copper acetate is 4 wt % Cu(II) acetate monohydrate in 3:1 TEGDMA/SP200
***** Copperacetate is 4 wt % Cu(II) acetate monohydrate in 1:1 TEGDMA/SP200

The accelerators consist of a diluent, an initiator molecule, and a peroxide (Table 7). The accelerator was prepared by adding all components into a small glass vial equipped with stirbar and stirring to ensure homogeneity.

TABLE 7

Accelerator Formulations 2 to 4 (A2 to A4)

| Component | A2 | A3 | A4 |
|---|---|---|---|
| BF9-88 | 2.63 g | 2.63 g | 2.63 g |
| PE 2 (b-PhDMBA) | 0.37 g | — | — |
| PE 3 (b-BnDMBA) | — | 0.38 g | — |
| PE 4 (cou-BnDMBA | — | — | 0.43 g |
| TBEC | 0.07 g | 0.07 g | 0.07 g |

Table 8 below demonstrates the use of PE 2-PE 4 as initiator compounds, Examples 7-20 (EX 7-20). Formulations were prepared by addition of 1.50 g applicable base resin (Table 5 or 6) and 0.15 g accelerator (Table 7) into a small glass vial and shaking for approximately 30 seconds to ensure homogeneity. Immediately afterwards, 1 drop of the mixed formulation was placed on a glass microscope slide (75×38×1.0 mm, from Fisher Scientific, Pittsburgh, PA) and covered with a microscope cover glass (22×22 mm, from Fisher Scientific, Pittsburgh, PA). When applicable, samples were irradiated using an LX-400 instrument (Lumen Dynamics, Mississauga, Ontario, Canada) equipped with a 365 nm LED lamp, holding the lamp within 1 centimeter (cm) of the surface of the cover glass for 30 seconds. Cure time was defined as the point at which the cover glass could no longer be moved by hand. Without irradiation, all mixed two-part formulations were stable for greater than 400 minutes. For EX 7-20, the brief irradiation was highly effective at triggering the redox cure.

TABLE 8

Examples 7-20 (EX 7-EX 20)

| | Initiator | Base resin, g | Accelerator, g | Cure time, no irradiation | Cure time, 30 seconds irradiation |
|---|---|---|---|---|---|
| EX 7 | PE 2 (b-PhDMBA) | B7, 1.5 | A2, 0.15 | >400 min | 38 min |
| EX 8 | PE 2 (b-PhDMBA) | B8, 1.5 | A2, 0.15 | >400 min | 40 min |
| EX 9 | PE 2 (b-PhDMBA) | B9, 1.5 | A2, 0.15 | >400 min | 40 min |
| EX 10 | PE 3 (b-BnDMBA) | B7, 1.5 | A3, 0.15 | >400 min | 25 min |
| EX 11 | PE 3 (b-BnDMBA) | B8, 1.5 | A3, 0.15 | >400 min | 27 min |
| EX 12 | PE 3 (b-BnDMBA) | B9, 1.5 | A3, 0.15 | >400 min | 29 min |
| EX 13 | PE 2 (b-PhDMBA) | B11, 1.5 | A2, 0.15 | >400 min | 6 min |
| EX 14 | PE 2 (b-PhDMBA) | B12, 1.5 | A2, 0.15 | >400 min | 7 min |
| EX 15 | PE 2 (b-PhDMBA) | B13, 1.5 | A2, 0.15 | >400 min | 7 min |
| EX 16 | PE 3 (b-BnDMBA) | B11, 1.5 | A3, 0.15 | >400 min | 12 min |
| EX 17 | PE 3 (b-BnDMBA) | B12, 1.5 | A3, 0.15 | >400 min | 9 min |
| EX 18 | PE 3 (b-BnDMBA) | B13, 1.5 | A3, 0.15 | >400 min | 10 min |
| EX 19 | PE 4 (cou-BnDMBA) | B10, 1.5 | A4, 0.15 | >400 min | 38 min |
| EX 20 | PE 4 (cou-BnDMBA) | B12, 1.5 | A4, 0.15 | >400 min | 42 min |

Synthesis of Reactive Oligomer A

Reactive Oligomer A was prepared generally according to the following procedure. 2EHA (12 g), 50 g of CHA, 30 g of BA, 5 g of Acm, 3 g of HPA, 0.1 g of VAZO-52, 0.1 g of TDDM, and 100 g of EtOAc were added to a glass bottle. The contents were mixed and bubbled with nitrogen for 4 minutes before being sealed and placed in a Launder-Ometer rotating water bath for 24 hours at 60° C. After 24 hours the sample was analyzed using GPC to determine $M_w$ and polydispersity index. In a second step, 0.52 g IEM and 40 g MEK were added to the bottle. The bottle was sealed with polytetrafluoroethylene tape, and rolled on an IR-lamp-heated roller designed to reach a temperature of 60° C. for 24 h. The weight average molecular weight of the resulting polymer was approximately 298 kD as determined by conventional gel permeation chromatography (GPC) methods. The GPC instrumentation, which was obtained from Waters Corporation (Milford, Massachusetts), included a high-pressure liquid chromatography pump (Model 1515HPLC), an auto-sampler (Model 717), a UV detector (Model 2487), and a refractive index detector (Model 2410). The chromatograph was equipped with two 5-micron PLgel MIXED-D columns, available from Varian Inc. (Palo Alto, California). The final determination was made by reference to polystyrene standards.

Test Methods

Overlap Shear Test Method Sample Preparation

A selected adhesive composition (in EtOAc/MEK solution) was coated onto the tight side of an RL1 siliconized polyester release liner and dried for 30 minutes in a solvent oven at 70° C. 1"×4"×0.064" (2.5 cm×10.2 cm×0.16 cm) aluminum substrates were prepared by scrubbing the terminal 1" (2.54 cm) with SCOTCH-BRITE GENERAL PURPOSE HAND PAD #7447 (3M) followed by washing with isopropanol and air-drying. A ½"×1" (1.3 cm×2.5 cm) portion of the adhesive composition was applied to the scrubbed end of one substrate. The release liner was removed, and the composition was exposed to UV from a D bulb microwave source (Heraeus Noblelight America, Gaithersburg, MD). The amount of radiation applied to each sample was 2.0 J/cm$^2$ in UVA, 0.5 J/cm$^2$ in UVB, 0.2 J/cm$^2$ in UVC, and 2.1 J/cm$^2$ in UVV as measured by an EIT PowerPuck II radiometer (EIT, Inc., Sterling, VA). A second substrate was applied to the irradiated sample, thus closing the bond (bond area %2"×1" (1.3 cm×2.5 cm)). The assembly was wet out by means of applying finger pressure. The bond was clamped with large binder clips and allowed to sit at room temperature for 18-24 hours prior to testing.

Dynamic Overlap Shear Test Method

A dynamic overlap shear test was performed at ambient temperature using an MODEL 55R1122 INSTRON TENSILE TESTER (Instron, Norwood, MA). Test specimens were loaded into the grips and the crosshead was operated at 0.1" (0.25 cm) per minute, loading the specimen to failure. Stress at break was recorded in units of psi and converted to pascals (or kilopascals). Three specimens of each sample were tested, and the average result calculated.

EXAMPLES

Example 21 (EX 21)

Tapes with Masked Barbituric Acid Derivatives

Each formulation in Table 9 (below) was assembled in a plastic cup and vigorously stirred by hand until homogeneous.

TABLE 9

Adhesive compositions for Example 21

| Formulation | Reactive Oligomer A (62 wt % in MEK) | MEK, g | CN1964, g | CHP, mg | TBEC, mg | Cu(naph)$_2$ in mineral spirits, mg | PE 1, mg |
|---|---|---|---|---|---|---|---|
| 21-A | 16.1 | 7.8 | 3.89 | 35 | — | 58 | 24 |
| 21-B | 16.1 | 7.8 | 3.89 | — | 56 | 58 | 24 |

Tape constructions and overlap shear samples from each of the above formulations were made according to the Overlap Shear Test Method Sample Preparation procedure above. The resulting samples were tested according to the Dynamic Overlap Shear Test Method above. The results of the tests are reported in Tables 10 and 11, in psi and kPa, respectively.

TABLE 10

Overlap shear test results for Example 21 (results in psi).

| Formulation | UV applied | OLS 1, psi | OLS 2, psi | OLS 3, psi | Average OLS strength, psi | Failure mode |
|---|---|---|---|---|---|---|
| 21-A | Yes | 1006 | 937 | 1067 | 1003 | Mixed adhesive |
| 21-A | No | 28 | 23 | 33 | 28 | Cohesive |
| 21-B | Yes | 920 | 786 | 644 | 783 | Mixed adhesive |
| 21-B | No | 14 | 14 | 14 | 14 | Cohesive |

TABLE 11

Overlap shear test results for Example 21 (results in kPa).

| Formulation | UV applied | OLS 1, kPa | OLS 2, kPa | OLS 3, kPa | Average OLS strength, kPa | Failure mode |
|---|---|---|---|---|---|---|
| 21-A | Yes | 6936 | 6460 | 7357 | 6915 | Mixed adhesive |
| 21-A | No | 193 | 159 | 228 | 193 | Cohesive |
| 21-B | Yes | 6343 | 5419 | 4440 | 5399 | Mixed adhesive |
| 21-B | No | 97 | 97 | 97 | 97 | Cohesive |

What is claimed is:

1. A polymerizable composition comprising a polymerizable component, and a redox initiation system comprising:
   a) a transition metal complex that participates in a redox cycle;
   b) an oxidizing agent;
   c) a photolabile reducing agent of the formula:

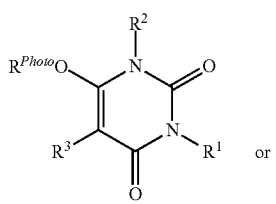

Ia

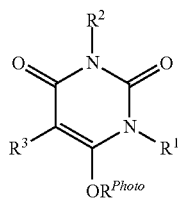

Ib wherein
   $R^1$, $R^2$ and $R^3$ are each independently H, $C_{1-18}$ hydrocarbyl; and
   a) $R^{Photo}$ is a photolabile group;
   and optionally a quaternary ammonium halide.

2. The polymerizable composition of claim 1, wherein the photolabile group $R^{photo}$ is selected from phenacyl groups, 2-alkylphenacyl groups, ethylene-bridged phenacyl groups, p-hydroxyphenacyl groups, benzoin groups, o- or p-nitrobenzyl groups, o-nitro-2-phenethyloxycarbonyl groups, coumarin-4-yl methyl groups, benzyl groups, o- or p-hydroxybenzyl groups, o- or p-hydroxynapthyl groups, 2,5-dihydroxyl benzyl groups, 9-phenylthioxanthyl, 9-phenylxanthyl groups, anthraquinon-2-yl groups, 8-halo-7-hydroxyquinoline-2-yl methyl groups, and pivaloylglycol groups.

3. The polymerizable composition of claim 1 wherein the transition metal complex is of the formula:

[ML$_p$]$^{n+}$A$^-$, wherein M is a transition metal that participates in a redox cycle, L is a ligand, A- is an anion, n is the formal charge on the transition metal having a whole number value of 1 to 7, and p is the number of ligands on the transition metal having a number value of 1 to 9.

4. The polymerizable composition of claim 3 wherein M is selected from Cu, Fe, Ru, Cr, Mo, Pd, Ni, Pt, Mn, Rh, Re, Co, V, Au, Nb and Ag.

5. The polymerizable composition of claim 1 wherein the redox initiator system is present in the composition in amounts, from 0.05 to about 10 parts by weight, based on 100 parts by weight of the polymerizable component of the polymerizable composition.

6. The polymerizable composition of claim 1 wherein further comprising a secondary reducing agent selected from tertiary amines; aromatic sulfinic salts; thioureas; and mixtures thereof.

7. The polymerizable composition of claim 1 wherein the oxidizing agent of the redox initiator system is selected from persulfuric acid and salts thereof; peroxides, hydroperoxides; transition metals, perboric acid and salts thereof, permanganic acid and salts thereof, perphosphoric acid and salts thereof, and mixtures thereof.

8. The polymerizable composition of claim 1 comprising more than one oxidizing agent.

9. The polymerizable composition of claim 1 wherein the polymerizable component comprises:
   i) 85 to 100 parts by weight of an (meth)acrylic acid ester;
   ii) 0 to 15 parts by weight of an acid functional ethylenically unsaturated monomer;
   iii) 0 to 10 parts by weight of a non-acid functional, ethylenically unsaturated polar monomer;
   iv) 0 to 5 parts vinyl monomer; and
   v) 0.1 to 5 parts of a multifunctional (meth)acrylate;
   vi) 0.1 to 10 parts by weight of the redox initiator system, based on 100 parts by weight of i) to v).

10. The polymerizable composition of claim 9 further comprising 0.01 to 5 parts of a multifunctional (meth)acrylate.

11. The polymerizable composition of claim 1 wherein the polymerizable component comprises:
   i) up to 100 parts by weight of an (meth)acrylic acid ester;
   ii) 0 to 15 parts by weight of an acid functional ethylenically unsaturated monomer;
   iii) 0 to 15 parts by weight of a non-acid functional, ethylenically unsaturated polar monomer;
   iv) 0 to 5 parts vinyl monomer;
   v) 0 to 100 parts of a multifunctional (meth)acrylate, relative to 100 parts i)-iv);
   and
   vii) the redox initiator system (including the transition metal complex, oxidant and photolabile reductant) in amounts from about 0.1 weight percent to about 5.0 weight percent, relative to 100 parts total monomer i)-v).

12. The polymerizable composition of claim 1 further comprising 1-35 parts by weight of a toughening agent, relative to 100 parts by weight of the polymerizable component of the polymerizable composition.

13. The polymerizable composition of claim 1 wherein the transition metal complex is Cu(II) naphthenate.

14. The polymerizable composition of claim 1, wherein the polymerizable ethylenically unsaturated component comprises a reactive oligomer having pendent polymerizable groups, and wherein the reactive oligomer comprises:
   a) greater than 50 parts by weight of (meth)acrylate ester monomer units;
   b) 0.5 to 10 parts by weight of monomer units having a pendent, free-radically polymerizable functional groups,
   c) 0 to 20 parts by weight of other polar monomer units, wherein the sum of the monomer units is 100 parts by weight.

15. A multilayer article comprising the polymerizable composition of claim 1 on a substrate.

16. The multilayer article of claim 15 wherein the substrate is a release liner.

17. The multilayer article of claim 15 wherein the substrate is a tape backing.

* * * * *

UNITED STATES PATENT AND TRADEMARK OFFICE
CERTIFICATE OF CORRECTION

| | |
|---|---|
| PATENT NO. | : 11,897,977 B2 |
| APPLICATION NO. | : 16/965688 |
| DATED | : February 13, 2024 |
| INVENTOR(S) | : William Harold Moser et al. |

It is certified that error appears in the above-identified patent and that said Letters Patent is hereby corrected as shown below:

In the Claims

<u>Column 31</u>
Line 41, In Claim 9, delete "v) 0.1 to 5 parts" and insert -- v) 0 to 5 parts --, therefor.

Signed and Sealed this
Twentieth Day of August, 2024

*Katherine Kelly Vidal*

Katherine Kelly Vidal
*Director of the United States Patent and Trademark Office*